US012582849B2

(12) United States Patent  
Ramamurthy

(10) Patent No.: US 12,582,849 B2  
(45) Date of Patent: Mar. 24, 2026

(54) DETERMINING ULTRASOUND-BASED BLOOD-BRAIN BARRIER OPENING OR INCREASED PERMEABILITY USING PHYSIOLOGIC SIGNALS

(71) Applicant: CORDANCE MEDICAL INC., Mountain View, CA (US)

(72) Inventor: Bhaskar Singenellore Ramamurthy, Los Altos, CA (US)

(73) Assignee: Cordance Medical Inc., Mountain View, CA (US)

( * ) Notice: Subject to any disclaimer, the term of this patent is extended or adjusted under 35 U.S.C. 154(b) by 0 days.

(21) Appl. No.: 18/947,293

(22) Filed: Nov. 14, 2024

(65) Prior Publication Data

US 2025/0152975 A1     May 15, 2025

Related U.S. Application Data

(60) Provisional application No. 63/599,082, filed on Nov. 15, 2023.

(51) Int. Cl.
| | |
|---|---|
| *A61N 7/02* | (2006.01) |
| *A61N 7/00* | (2006.01) |
| *G16H 40/63* | (2018.01) |

(52) U.S. Cl.
CPC ............... *A61N 7/02* (2013.01); *G16H 40/63* (2018.01); *A61N 2007/0021* (2013.01); *A61N 2007/0039* (2013.01)

(58) Field of Classification Search
CPC .... A61N 7/00; A61N 7/02; A61N 2007/0021; A61N 2007/0039; A61B 5/369; A61B 5/377; G06F 3/015
See application file for complete search history.

(56) References Cited

U.S. PATENT DOCUMENTS

| | | | |
|---|---|---|---|
| 11,534,630 | B2 | 12/2022 | Ramamurthy |
| 11,627,936 | B2 | 4/2023 | Ramamurthy |
| 11,857,812 | B2 | 1/2024 | Ramamurthy |
| 12,017,093 | B2 | 6/2024 | Ramamurthy et al. |
| 2019/0183457 | A1 | 6/2019 | Ramamurthy |
| 2019/0184204 | A1* | 6/2019 | Ramamurthy ......... A61B 8/481 |
| 2023/0082109 | A1 | 3/2023 | Ramamurthy et al. |
| 2023/0128189 | A1 | 4/2023 | Ramamurthy |
| 2024/0033541 | A1 | 2/2024 | Ramamurthy et al. |

(Continued)

FOREIGN PATENT DOCUMENTS

| | | |
|---|---|---|
| WO | 2024/238674 A2 | 11/2024 |

OTHER PUBLICATIONS

Kiviniemi, Vesa, et al. "Real-time monitoring of human blood-brain barrier disruption." PloS one 12.3 (2017): e0174072.*

*Primary Examiner* — Carolyn A Pehlke

(74) *Attorney, Agent, or Firm* — Dicke, Billig & Czaja, PLLC

(57) ABSTRACT

Examples are directed to devices, methods, and systems for determining opening or increased permeability of a blood-brain barrier (BBB) of a patient. An example device comprises memory circuitry that stores a set of non-transitory instructions, and processor circuitry coupled to the memory circuitry and configured to execute the instructions to determine opening or increased permeability of a BBB of a patient during an ultrasound-based BBB opening procedure using physiologic signals obtained from the patient.

20 Claims, 7 Drawing Sheets

(56) References Cited

U.S. PATENT DOCUMENTS

| | | | |
|---|---|---|---|
| 2024/0042242 A1 | 2/2024 | Ramamurthy et al. | |
| 2024/0130663 A1* | 4/2024 | Myllylä | A61B 5/4064 |
| 2024/0307709 A1 | 9/2024 | Ramamurthy et al. | |

* cited by examiner

DETERMINING ULTRASOUND-BASED BLOOD-BRAIN BARRIER OPENING OR INCREASED PERMEABILITY USING PHYSIOLOGIC SIGNALS

RELATED APPLICATION

This Application claims the benefit of U.S. Provisional Application 63/599,082, filed on Nov. 15, 2023, hereby incorporated herein in its entirety by reference.

BACKGROUND

Focused ultrasound can be used to safely open or increase the permeability the blood-brain barrier (BBB) temporarily. The advantages of increased permeability of the BBB include the ability to deliver drugs to the diseased tissue within the brain and the ability to perform liquid biopsy for brain diseases as disease biomarkers can migrate into the blood from the brain tissue. Sampling of blood can be accomplished at a peripheral site, such as the arms; subsequently, the blood from the brain tissue can be analyzed for the presence of biomarkers which can indicate the status of disease within the brain. Successfully opening and verifying opening of the BBB can be difficult due to the anatomy of the skull and brain tissue. Accordingly, there remains a need for efficient techniques for verifying opening of the BBB.

DETAILED DESCRIPTION

Figure 1:
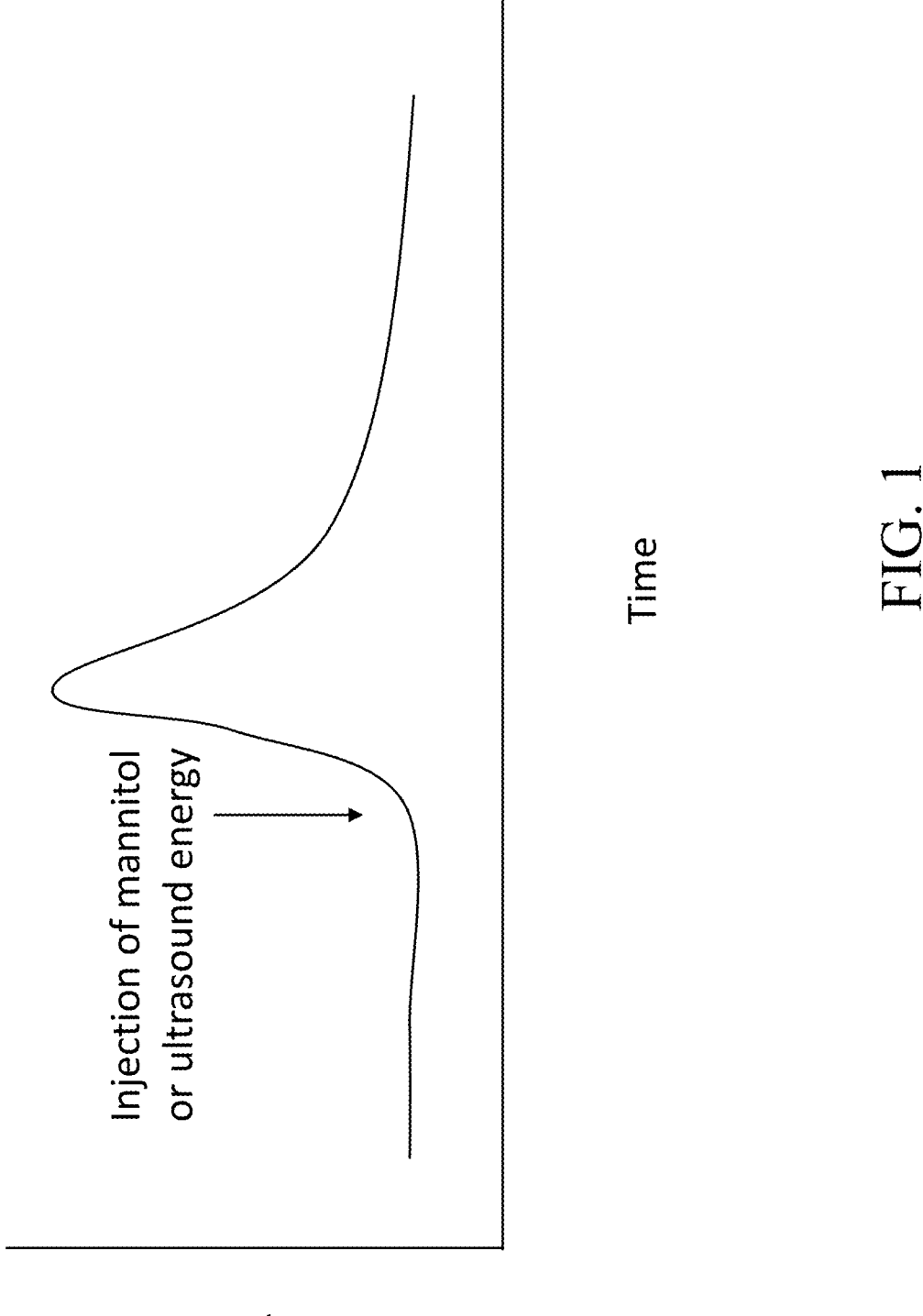
FIG. 1 illustrates example changes in a physiologic signal from a baseline level in response to an ultrasound-based BBB opening procedure, according to examples of the present disclosure.

Aspects of the present disclosure are directed to a variety of methods, devices, and systems for determining when the blood-brain barrier (BBB) opens during an ultrasound-based BBB opening procedure, which optionally includes an ultrasound-based BBB opening procedure. In some examples, physiologic signals may be obtained and used to control the sonication procedure. For example, the methods may be performed using and/or a system may include a focus ultrasound system (FUS) used to perform the ultrasound-based BBB opening procedure, where the ultrasound-based BBB opening procedure is controlled as a result of the physiologic signals. More specifically, the ultrasound-based BBB opening procedure may continue and/or may be stopped depending on the physiologic signals which are obtained while a patient is undergoing the ultrasound-based BBB opening procedure. In some examples, baseline physiologic signals are compared to physiologic signals obtained during the ultrasound-based BBB opening procedure to verify opening of the BBB. For example, changes in the physiologic signals from the baseline may confirm the BBB is open. While the present invention is not necessarily limited to such applications, various aspects of the invention may be appreciated through a discussion of various examples using this context.

In an ultrasound-based BBB opening procedure, typically ultrasound is focused into a selected part of the brain while an ultrasound contrast agent is injected into the patient though an intravenous procedure. The ultrasound contrast agent is typically made up of small microbubbles. Several such microbubbles are available commercially. The microbubbles typically are made of thin lipid shells with an inert gas. The microbubbles reflect ultrasound energy; the reflected energy contains information about how violently the bubbles are vibrating or oscillating within the vasculature. Bubbles vibrating in a "stable cavitation mode" typically results in a temporary stretching of the vascular walls. In this state, the intracellular spaces between the endothelial cells that make up the vascular walls open temporarily—this phenomenon is called "opening of the blood-brain barrier". However, it may be appreciated that the BBB opening process is not necessarily a binary event but may happen over a period of time such as one to three minutes. As such, the BBB opening process may be described as increasing the permeability of the BBB. Typically, the BBB is permeable to very few substances (e.g. nutrients and waste products). The permeability to large molecules (e.g. greater than 150 kilodalton (kDa)) is non-existent or poor. The permeability may be increased by the ultrasound-based BBB opening procedure and may result in opening of the BBB. During the ultrasound-based BBB opening procedure, the permeability may increase gradually over time e.g. over the period of time of one to three minutes. After this time period, depending on the parameters used for the ultrasound-based BBB opening procedure, the BBB may allow molecules with molecular weights such as 150 kDa to pass through but may not allow larger molecules to pass through (such as those with molecular weights greater than 200 kDa). As used herein, the term "opening the BBB" may refer to an instant of time when the BBB is open and/or it may refer to a period of time after which the permeability has increased sufficiently to allow substances that typically do not cross the BBB, to pass through, sometimes herein referred to as "increased permeability".

Bubbles vibrating in an "inertial cavitation mode" typically result in damage to vascular structure, which is not desirable. In the stable cavitation mode, signals reflected back from the bubbles are more orderly or organized in that if the signals are analyzed in the frequency domain, harmonics, sub-harmonics, or ultra-harmonics are observed. If bubbles are vibrating in the inertial cavitation mode, an increased in the overall noise level is seen in the frequency spectrum. Thus, it is possible to receive the signals reflected back from the bubbles and determine the mode of vibration.

However, analysis of the echo signals from the microbubbles may be confounded by several factors. In some configurations, the transducer that includes elements capable of receiving echo signals, are placed outside the skull. The skull attenuates the already weak echo signals from the microbubbles. This makes detection of signals challenging. In some cases, intervening media between the transducer and the brain target tissue can create signals in the same frequency band as the echo signals are expected to be in. In such cases, it can be challenging to distinguish signals from microbubbles versus from other media.

The microbubble oscillations are dependent on the in-situ acoustic pressure experienced by brain tissue as a result of ultrasound transmission into the brain. Thus, it is possible to control the microbubble oscillations. The return signals from the microbubbles may be analyzed and results can be used to modulate or control the excitation voltage of the transmitting elements in the transducer. For this feedback loop between analysis of the echo signals and excitation voltage of the transmitters to be robust, the echo signals should be robust and the analysis of these signals should also be robust. The challenges outlined above affects this robustness. As further described herein, various examples are directed identifying when the BBB has opened using feedback, such as physiologic signals obtained during the ultrasound-based BBB opening procedure. In some examples, the method can be used in a feedback loop to control the excitation voltage associated with the ultrasound-based BBB opening procedure. Additionally, the physiological signal feedback can be used alone or in combination with microbubble-based feedback to increase safety of the ultrasound-based BBB opening procedure.

In some examples, the physiologic signal used as feedback can include electroencephalogram (EEG) signals. The brain is a highly complex organ; for example, among the various tissues that make up the brain is a mass of neurons. It is estimated that the human brain contains about 86 billion neurons. Every region of the brain is known to contain neurons albeit in varying densities. Neurons or nerve cells are the essential parts of the nervous system. These cells are responsible for communication within the brain, the spinal cord and the rest of the body. These cells achieve this functionality by transporting and processing electrical and chemical signals. The electrical activity of these neurons creates EEG signals which can be detected on the scalp. These signals, recorded by placing electrodes on the head such as on the scalp, provide information about the gross or overall electrical activity of the brain.

EEG signals typically contain oscillatory signals at different frequency bands. Each band of signals are associated with different types of activity. Delta waves ranging from about 0.5 to 4 hertz (Hz) are typically associated with deep sleep, unconsciousness, and brain abnormalities. Theta waves ranging from about 4 to 8 Hz are typically associated with drowsiness, early stages of sleep etc. Alpha waves ranging from about 8 to 13 Hz are associated with wakefulness but relaxed state. Beta waves ranging from 13 to 30 Hz are typically associated with wakefulness, active thinking etc. Gamma waves ranging above 30 Hz are associated with cognition processing, sensory perception etc.

While neuronal activity is the main source of the EEG signals, non-neuronal sources can also contribute to the EEG activity. Some examples of non-neuronal sources include muscle activity, changes on blood flow or vascular activity etc.

In addition to the EEG signals in the frequency bands described above, some EEG signals can exist at even lower frequencies less than 0.5 Hz (e.g. approximately between 0.01 to 0.15 Hz). Potential sources of these EEG signals include fluctuations in blood flow, changes in cerebral perfusion or alterations in neurochemical concentrations within the brain. The signals at these very low frequencies (VLF) may be measured using a technique called Direct Current Electroencephalography (DC-EEG).

The BBB is a highly selective barrier that does not allow free passage of substances, such as drugs or biomarkers between the blood in the vascular structures (e.g. capillaries) and the brain tissue. This makes diagnosis (e.g. through liquid biopsy) and therapy (e.g. through delivery of drugs) challenging. One method to overcome the challenge of the blood-brain barrier is to inject the patient with a drug called mannitol. This drug is typically injected intra-arterially. Mannitol is a hyperosmolar agent and it induces the BBB to open by causing osmotic shrinkage of the endothelial cells that make up the BBB. This method of opening the BBB poses a significant risk to the patients as the opening of the BBB may be global (e.g. throughout the brain rather than only at or around a diseased area). Research has shown that opening the BBB with Mannitol can result in changes to the VLF EEG signals as monitored by the DC-EEG technique, such as described by, V. Kiviniemi et al., Real-time monitoring of human blood-brain barrier disruption, PLOS ONE, vol. 12, no. 3, p. e0174072, March 2017, and which is incorporated herein in its entirety for its teaching. FIG. 1 depicts this effect. In FIG. 1, the EEG is shown starting from a baseline level. Then mannitol is injected into the patient. The EEG increases in value from the baseline, reaching a maximum value and then decreases over time, returning to the baseline level. As further described below and illustrated by FIG. 1, ultrasound energy from a FUS can alternatively and/or additionally result in a change in EEG from the baseline. While FIG. 1 illustrates the ultrasound energy delivered at an instant of time, the ultrasound energy may be delivered over a period of time (such as in 10 ms); further it may be delivered in multiple sonication bursts over a period of time (e.g. over the sonication duration).

FIG. 1 illustrates example changes in a physiologic signal from a baseline level in response to an ultrasound-based BBB opening procedure, according to examples of the present disclosure. In some examples, an ultrasound-based BBB opening procedure is used to open the BBB (using a FUS) while the EEG is monitored (using an EEG system). When the BBB is opened or otherwise has increased permeability, some components of blood, specifically plasma, albumin etc., can pass through the open BBB. This changes the neurochemical environment around the location where BBB is opened. Such changes in the neurochemical environment may induce a change in the EEG as measured on an external location, such as the scalp. If the EEG is monitored prior to and throughout the ultrasound-based BBB opening procedure with FUS, any changes in the EEG when the ultrasound is being applied, may imply that the BBB has opened or has increased permeability and some of the components of the blood has traveled outside the vasculature and into the brain tissue. Thus, the changes in EEG can be monitored and may be used in a control scheme to stop or otherwise control the ultrasound-based BBB opening procedure. In some examples, the technique may provide a way optimize sonication time. It may also increase the safety of the ultrasound-based BBB opening procedure. Examples of controlling the ultrasound-based BBB opening procedure are not limited to the above examples and may include stopping the ultrasound-based BBB opening procedure prior to the (preprogrammed) sonication duration, continuing the ultrasound-based BBB opening procedure through the end of the (preprogrammed) sonication duration, extending the (preprogrammed) sonication duration, and/or adjusting other sonication parameters, such as the excitation voltage, and burst time (e.g. $T_{on}$ and/or $T_{off}$).

Figure 2:
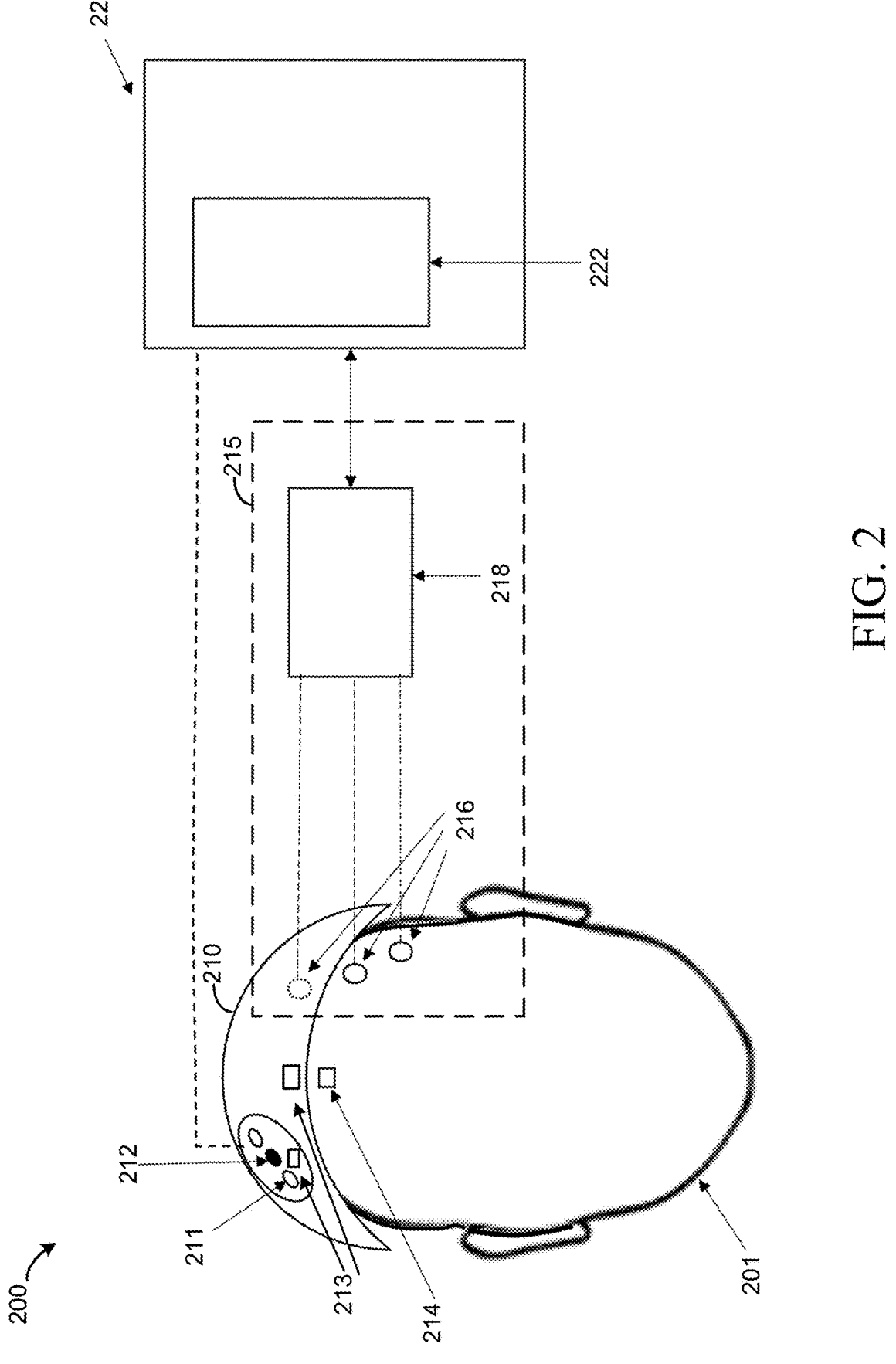
FIG. 2 illustrates an example system including a focused ultrasound system (FUS) and an electroencephalography (EEG) system.

FIG. 2 illustrates an example system including a FUS and an EEG system, according to examples of the present disclosure. The system 200 may capture the EEG signals or other physiologic signals emanating from the head of the patient 201. As described above, the FUS 220 may be used to open the BBB using an ultrasound-based BBB opening procedure, which may be referred to as a "sonication procedure" or a "FUS-based BBB opening procedure". The EEG system 215 can include sensors 216 (e.g. EEG sensors) and an EEG analyzer 218. The EEG system 215 may be used to obtain EEG signals used to control the operation of the FUS 220 including the sonication time that is required to open the BBB. In FIG. 2, the patient 201 is shown wearing a cap-like device 210 (herein sometimes referred to as a "cap" for ease of reference) over the head. The cap 210, which is part of the FUS 220, may include one or multiple types of transducers 211, 212. Further, each type of transducer 211, 212 may include multiple elements. One type of transducer, sometimes herein referred to as "the therapy transducer 211", may operate at low-frequency transducer and may be responsible for BBB opening. The low-frequency may be in the range of 250 kilohertz (kHz) to 1.5 megahertz (MHz). A second type of transducer, sometimes herein referred to as "the monitoring transducer 212", may be optionally included. The monitoring transducer 212 may be used to receive the signals reflecting back from the structures of the brain and/or from agents, such as ultrasonic contrast agents (e.g. microbubbles) (intentionally) injected into the patient 201. The signals from the monitoring transducer 212 may be used to control the excitation voltage applied to the therapy transducer 211. The elements of the transducer(s) 211, 212 may cover small or large sections of the head (e.g. the cap 210 may be populated with variable number of elements).

As shown by FIG. 2, the system 200 may further include sensors 214, 216 that are attached to the patient 201. One or several types of sensors 214, 216 may be attached. One type of sensor 216 may be an EEG sensor, which may include electrode(s) and electrical connection between the electrode(s) and circuitry. Several types of EEG sensors are commercially available and may be used. As an example, EEG sensors may be placed on the scalp or on the temples of the patient or on other locations on the head and face. In some examples, over the ear sensors may be used. These sensors 214, 216 may be attached to the patient 201 with biocompatible adhesive and may be removed after use. The signals from the EEG sensors (e.g. 216) may be analyzed by the EEG analyzer 218. In some examples, the EEG electrodes or sensors 216 and the EEG analyzer 218 may form at least part of and/or be referred to as the EEG system 215, which may optionally further include additional circuitry (e.g. controller or other processor, and/or communication circuitry).

Example are not limited to those described above. For example, sensors 216 may not be limited to EEG sensors and/or may capture physiologic signals other than EEG signals. Similarly, the EEG analyzer 218 may include processor circuitry configured to process physiological signals in addition to or alternatively to the EEG signals. Furthermore, the physiologic signals can be analyzed by circuitry other than the EEG analyzer 218, such as a separate processor, a physiological signal analyzer, and/or processor circuitry of the FUS 220 (e.g. controller 222). The EEG analyzer 218 or other physiologic signal analyzer can include a device or component of a device including at least processor circuitry, and optionally memory circuitry, among other components as further described herein.

Additionally, the system 200 may include other sensors 213, 214 which form part of the cap 210 or are separate from the cap and attached to the patient 201. The other sensors 213, 214 may include motion sensors, among other types of sensors. The sensors 213, 214, for example, may be electromagnetic 6 degree-of-freedom (DOF) position sensors, or sensors that measure acceleration, orientation, angular rates (typically called inertial measurement units). These sensors 213, 214 may be used to determine the relative position of the cap 210 with respect to head of the patient 201, such as described in U.S. Pat. No. 11,534,630 which is incorporated by reference in its entirety for its teaching.

As shown by FIG. 2, the system 200 may further include a master controller 222, which may reside within the FUS 220 or be separate therefrom. The master controller 222 may include at least processor circuitry and memory circuitry, as further described herein. The master controller 222 may enable a two-way communication channel between the FUS 220 and the EEG system 215 (or other physiologic signal system). The master controller 222 may control the operation of the FUS 220 and the EEG system 215. The EEG system 215 may be controlled via the two-way communication channel. The two-way communication channel may transfer control information and EEG data. In some examples, the acquisition of the EEG signals may be started and stopped with commands through the communication channel. The EEG analyzer 218 of the EEG system 215 may send digital or analog EEG signals to the FUS 220 through the two-way communication channel. If analog data is sent, then an analog-to-digital converter may be included as part of the FUS 220 and/or as part of the master controller 222. This is not shown in FIG. 2 for ease of reference. A suitable sampling frequency, such as 120 Hz (typically 4 times above the highest frequency expected), may be used.

In accordance with various examples, the digitized EEG signals are processed within the master controller 222. In some examples, the master controller 222 may include a computer device, e.g. a microprocessor, which is capable of analyzing data. The computing environment may also include digital memory to store EEG data or processed data based on the EEG signals. As used herein, the EEG data or the processed data based on the EEG is referred to as "EEG data". The EEG data may be analyzed within the computing environment, which may include the master controller 222 and optionally other components, such as circuitry of the EEG analyzer 218. The computing environment may be able to digitally filter the EEG data and analyze the data for one or several frequency bands. The filtered data may be compared to EEG data already stored in the memory.

Figure 3:
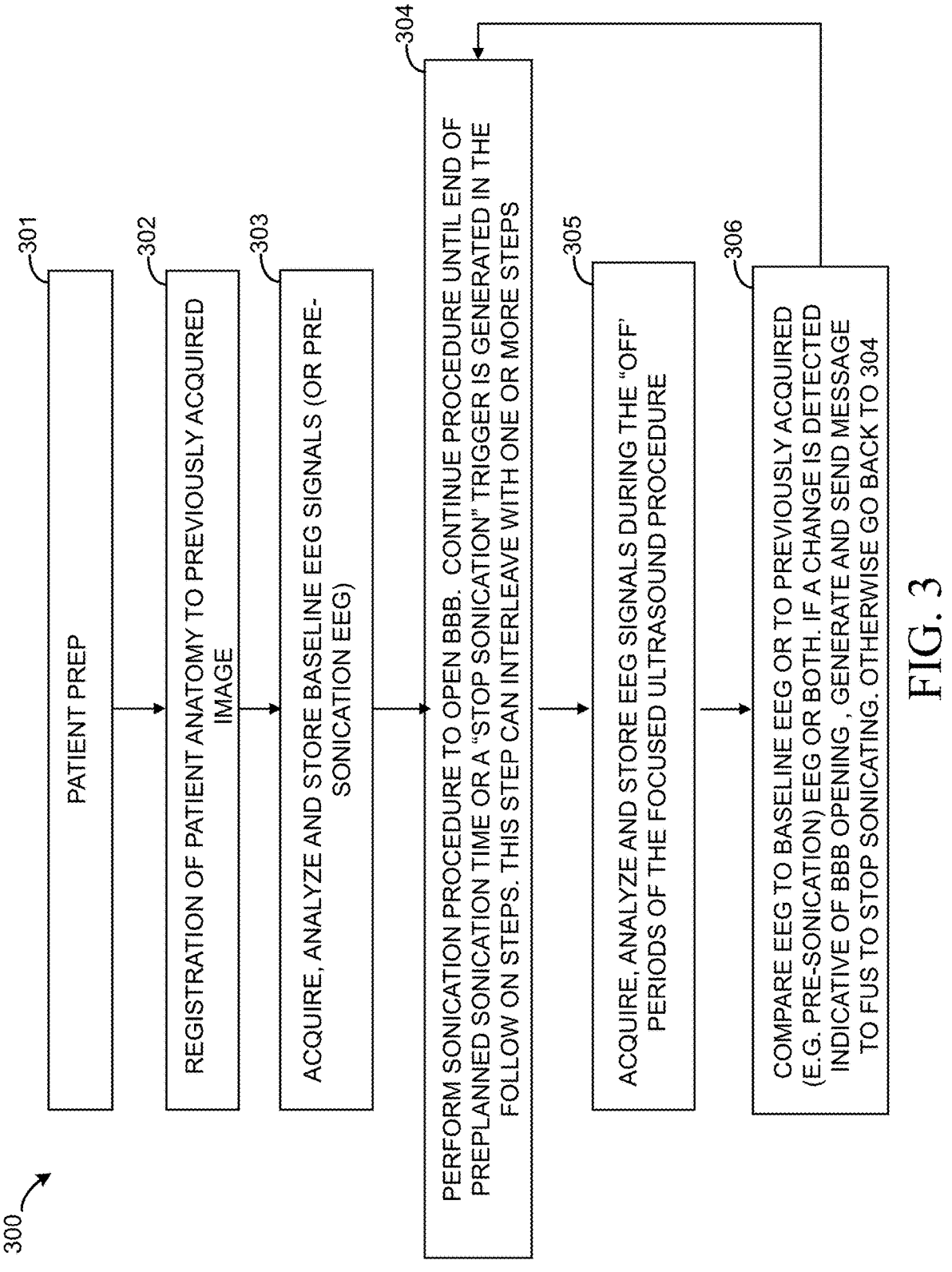
FIG. 3 is a flow chart of an example method of operating the FUS and EEG system shown in FIG. 2, according to examples of the present disclosure.

FIG. 3 is a flow chart of an example method of operating the FUS and EEG system shown in FIG. 2. Some portions (e.g. steps) of the method 300 may overlap with others and the order may be different than illustrated by the flow chart of FIG. 3. At 301, the patient is prepared. In some example, the patient may be prepared by situating the patient in a chair or bed, placing the EEG sensors and/or other types of sensors on the patient, placing the cap on top of the patient's head, etc. In some examples, the method 300 may include accepting data or information from procedures prior to preparing the patient, at 301. Specifically, a magnetic resonance imaging (MRI) or computer tomography (CT) scan may be performed previously. Such image(s), called "preacquired images" may have been acquired hours or days prior to start of preparing the patient. In some examples, preparing the patient may also include specification of a region of interest (ROI) where the BBB is to be opened. The ROI may be specified by a physician, for example, based on the pre-acquired images.

The method 300, at 302, may include registering the patient's anatomy to the previously acquired images. The registration procedure may ensure that the cap location, after placement on the patient's head, which may be measured in relation to the patient's anatomy. This further ensures that the appropriate elements of the therapy transducer may be activated such that when activated, the ultrasound beams are able to reach the intended target or the ROI within the brain of the patient. The registration procedure may ensure that the coordinate(s) of the ROI as specified in the previously acquired images is transformed into the coordinates the FUS is using.

At 303, the method 300 includes capturing the physiologic signals from the EEG sensors and analyzing the physiologic signals prior to the start of ultrasound-based BBB opening procedure or sequence intended to open the BBB. These EEG signals may be referred to as "pre-sonication EEG signal" or "baseline EEG signal". In some examples, the pre-sonication EEG patterns are stored and may be used in later steps to determine a change in EEG during the ultrasound-based BBB opening procedure.

At 304, the ultrasound-based BBB opening procedure is commenced to open the BBB. The ultrasound-based BBB opening procedure may include a set of transmissions in a sequence 400, such as shown in FIG. 4 as an example.

Figure 4:
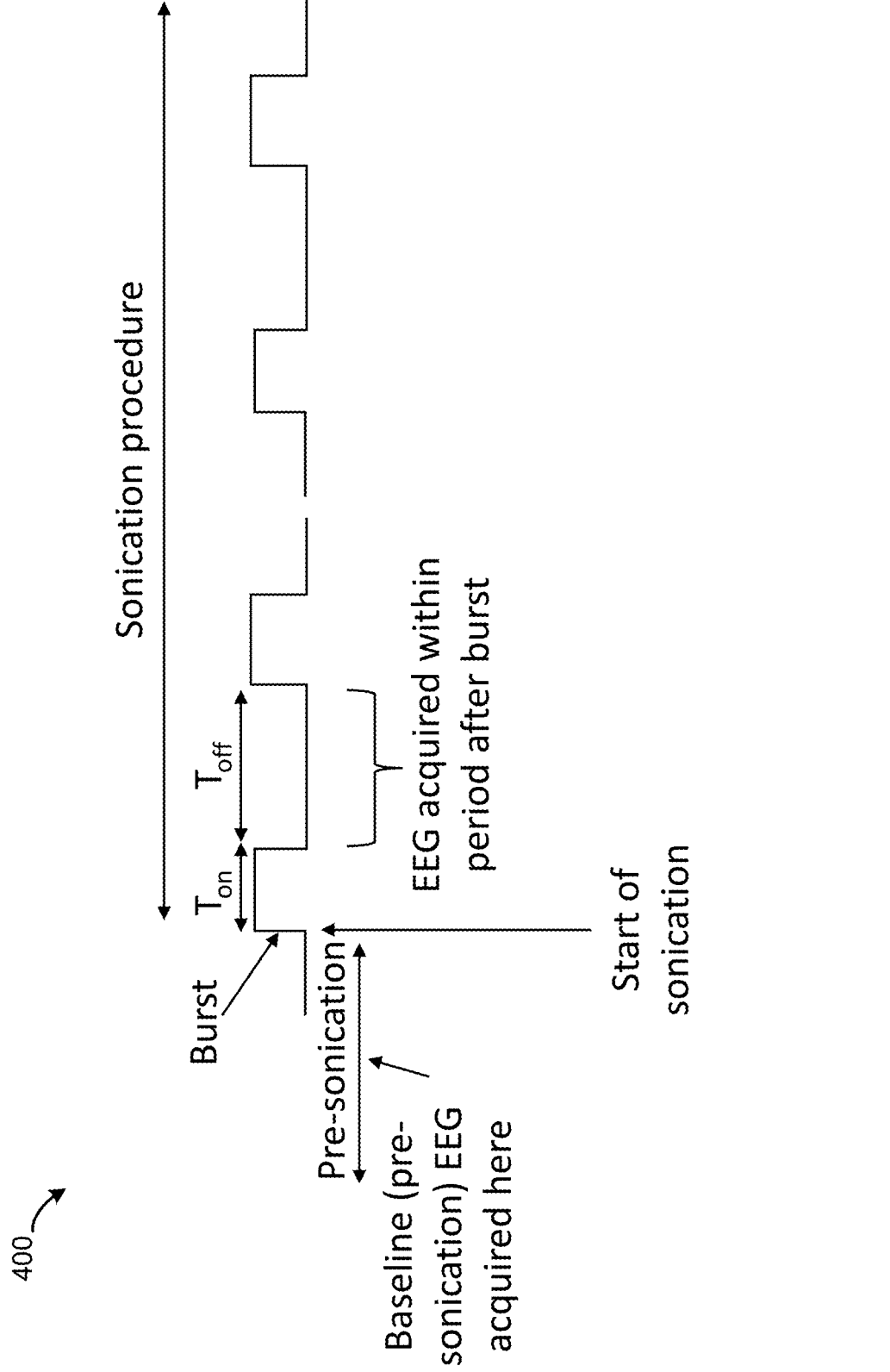
FIG. 4 illustrates an example timing diagram, according to examples of the present disclosure.

FIG. 4 illustrates an example timing diagram. Referring to FIG. 4, sonication is applied in a series of bursts (which are sometimes herein interchangeably referred to as "sonication bursts"). Within each burst, some or all of the low-frequency transducers, such as those shown by FIG. 2, are activated. The transducers, when activated, emit ultrasound energy at a specific frequency, such as 250 kHz. The transducers continue to emit ultrasound at this frequency for the duration of the burst ($T_{on}$). For focusing the ultrasound energy at a desired location, each activated transducer may be excited with a specific phase such that the ultrasound energy from the activated transducers arrive at the desired location (or the ROI) at the same time. If the in-situ acoustic pressure is above a threshold, in certain conditions (e.g. when microbubbles, an ultrasound contrast agent is present within the bloodstream of the patient), the BBB temporarily opens. In some examples, the ultrasound-based BBB opening procedure can be implemented using at least some of substantially the same features and attributes as described in U.S. Pat. No. 11,534,630, issued on Dec. 27, 2022, and entitled "Ultrasound Guided Opening of Blood-Brain Barrier", which is hereby incorporated by reference in its entirety for its teaching. During the $T_{off}$ period, no bursts or sonications are applied. Typically for the ultrasound-based BBB opening procedure, the $T_{on}$ time is 10 milliseconds (ms) and the $T_{off}$ period is 990 ms. The sonication duration of the ultrasound-based BBB opening procedure refers to the total length of time the cycle(s) of $T_{on}$ and $T_{off}$, and may include multiple cycles and may be applied repeatedly. Typically, the sonication duration of the ultrasound-based BBB opening procedure is three minutes, however it may be shortened by other processes or conditions as described herein.

Referring back to FIG. 3, at 305, the EEG signal is acquired, analyzed and stored during the "off" periods as further shown in FIG. 4. And, at 306, after every burst of sonication and preferably prior to the start of the next burst, the most recent EEG signal is compared to the baseline EEG signal, the previous EEG signal(s) acquired after every burst, or both. Changes in the most recent EEG signal relative to the baseline EEG signal or the previously acquired one or multiple EEG signals acquired after every burst, may signify that the BBB has opened. In some examples, when such a change is detected, then the sonication procedure may be stopped. In some examples, if changes in EEG are not detected even at the end of the duration of the ultrasound-based BBB opening procedure, the ultrasound-based BBB opening procedure may be extended on a burst-by-burst basis or on a multiple burst basis. In each case (burst-by-burst or multiple burst case), the EEG is analyzed as described above with a decision being made to stop or continue. There also may a high limit such that the extension of the ultrasound-based BBB opening procedure cannot exceed the maximum limit such as five or ten minutes.

As described above, the EEG change indicative of BBB opening may appear only in certain frequency bands such as in the VLF band. Thus, in some examples, the analysis that may be accomplished by the master controller and the associated computing environment may monitor energy in specific predefined bands of frequency within the EEG spectrum. If, for example, in the VLF band, the energy increases (or spikes) after a burst compared to the energy that was present either at the pre-sonication time (e.g. baseline EEG signal) or after a previous burst or both, then the spike may be indicative of the BBB opening as a result of the burst.

To accomplish the analysis, the digitized EEG signals may be processed by the EEG analyzer and/or the master controller in the following manner as an example:

(i) The Fast Fourier Transform of the EEG signals may be first calculated;

(ii) The frequency spectrum may be divided into one or multiple bins, each bin with a predetermined, user defined width (e.g. 0.5 Hz);

(iii) The energy in each bin may be summed and associated with that bin. For example, the energy for bin 1 which may extend from 0 to 0.5 Hz may be E1; the energy in bin 2 which may extend from 0.5 H to 1 H may be E2 etc. These energy values may be stored and indexed by the burst number and type. For example, the energy values may be stored according to the index Pre-sonication Burst 1, Pre-sonication Burst 2, Sonication Burst 1, Sonication Burst 2 etc.;

(iv) The energy values for each bin across multiple pre-sonication bursts may be averaged and this may be used as a "reference values" in other steps in the analysis.

(v) Then during the ultrasound-based BBB opening procedure after each burst, the same process as above is followed however now the energy value in each bin may be compared to the reference values.

(vi) Now to make a determination if the change in the EEG was caused by the BBB opening, a set of comparisons or logic may be applied. An example is provided below:

a. If the energy in the bins after a burst is different (higher or lower) across multiple frequency bins as compared to the pre-sonication energy in the corresponding bins, then it is likely that the change was caused by some other phenomenon not associated with BBB opening.

b. If the energy in the bins after a burst is higher in the VLF band (0 Hz to 0.5 Hz) and the energy in all other bins remained relatively the same (i.e. within a threshold, e.g. +/-1 dB), then it may be concluded that the change was caused by BBB opening.

(vii) If the determination is made that the BBB is opened, then the master controller may stop further bursts prior to conclusion of the full preprogrammed sonication duration. If the determination is made that the BBB is not opened, then the master controller may allow further bursts until the end of the preprogrammed sonication duration. In some cases, the master controller may extend the ultrasound-based BBB opening procedure until a maximum higher limit (e.g. 5 mins or 10 mins).

The above-described methods, devices, systems, and techniques are not limited to that illustrated by FIGS. 1-4. Examples of present disclosure are directed to use of physiologic signals other than EEG signals. Other example physiologic signals and processing techniques include magneto-encephalography (MEG) (e.g. measuring changes in the magnetic field produced by the brain's electrical activity, which may be referred to as MEG signals), electrocorticography (ECoG) (e.g. measuring changes in electrical activity in the brain, which may be referred to as ECoG signals), and ultrasonography (e.g. changes in gray scale imaging data or changes in blood flow, which may be electrical signals). Accordingly, in some examples, the physiologic signals may include EEG signals, MEG signals, ECoG signals, electrical signals, or various combinations thereof, as well as other signals captured from the head of the patient. Additionally, data processing is not limited to an EEG analyzer and separate master controller on or off the FUS. In some examples, all data is processed by a master controller, such that the system does not include an EEG analyzer or other type of physiologic signal analyzer. In some examples, a device separate from the FUS and/or EEG system is used to process the data and control the FUS and/or EEG system. Examples include other variations.

Figure 5:
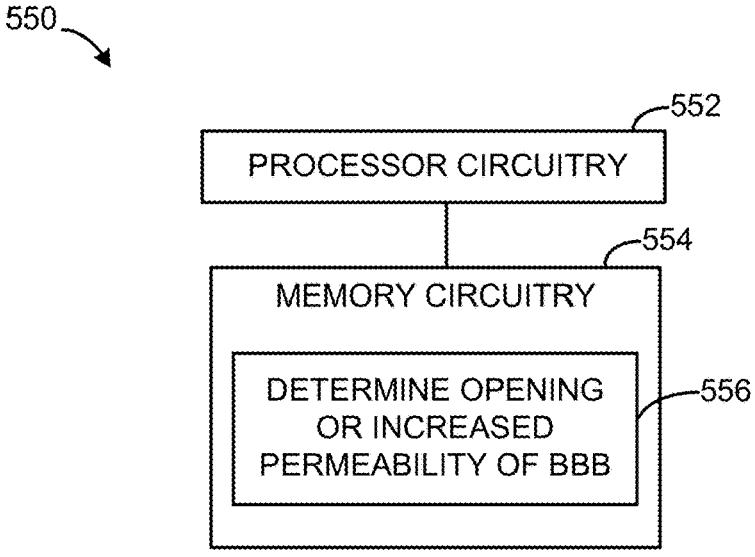
FIG. 5 illustrates an example device configured to determine opening or increased permeability of the BBB using physiologic signals, according to examples of the present disclosure.

FIG. 5 illustrates an example device configured to determine opening or increased permeability of the BBB using physiologic signals, according to examples of the present disclosure. The device 550 may form part of the FUS 220 of FIG. 2, part of the EEG analyzer 218 (or other physiologic signal analyzer) of FIG. 2, may form part of a separate device from the FUS 220 and the EEG analyzer 218, may be distributed among the FUS 220 and EEG analyzer 218, or may be distributed among the FUS 220, EEG analyzer 218, and a separate device from the FUS 220 and EEG analyzer 218. For example, resources of the device 550 (e.g. processor circuitry 552 and memory circuitry 554) can be distributed on the FUS 220, the EEG analyzer 218 or system 215, and/or a separate device, such as via a Cloud-computing system. In some examples, the processor circuitry 552 and memory circuitry 554 may form part of computing device(s) which are local to or remotely located to the FUS 220 and EEG system 215.

As shown by FIG. 5, the device 550 includes processor circuitry 552 and memory circuitry 554. The memory circuitry 554 may include a computer-readable storage medium storing a set of instructions 556. The memory circuitry 554 may include Read-Only Memory (ROM), Random-Access Memory (RAM), Electrically Erasable Programmable Read-Only Memory (EEPROM), flash memory, a solid state drive, Electrically Programmable Read Only Memory aka write once memory (EPROM), physical fuses and e-fuses, and/or discrete data register sets. In some examples, memory circuitry 554 may be a non-transitory storage medium, where the term "non-transitory" does not encompass transitory propagating signals. The processor circuitry 552 may be coupled to the memory circuitry 554 to execute the instructions 556 to perform the actions, as further described below. As described above, the processor circuitry 552 and/or memory circuitry 554 may include a plurality of circuits (e.g. processor circuits, memory circuits) which are distributed on different systems and/or devices.

At 556, the processor circuitry 552 may determine opening or increased permeability of a BBB of a patient during an ultrasound-based BBB opening procedure using physiologic signals obtained from the patient. As described above, the physiologic signals may be obtained from sensor(s), which capture the physiologic signals from the patient and are provided to the processor circuitry 552 from sensor(s) or other circuitry. In some examples, the processor circuitry 552 may determine the opening or the increased permeability of the BBB using the physiologic signals of the patient, at least portions of which are obtained while the patient is undergoing the ultrasound-based BBB opening procedure performed by and/or using a FUS. In some examples, the physiologic signals are EEG signals, however examples are not so limited.

The physiologic signals can be obtained at different times. For example, the processor circuitry 552 (in combination with sensors and/or a physiologic signal system) may obtain at least portions of the physiologic signals during the ultrasound-based BBB opening procedure between sonication bursts of the ultrasound-based BBB opening procedure. In some examples, the processor circuitry 552 may obtain at least portions of the physiologic signals prior to the ultrasound-based BBB opening procedure and during the ultrasound-based BBB opening procedure. The physiologic signals may be obtained as previously described at least in connection with FIG. 4 and via sensors as described in connection with FIG. 2.

In some examples, the processor circuitry 552 may obtain a baseline physiologic signal prior to the ultrasound-based BBB opening procedure and use the baseline physiologic signal to determine opening or increased permeability of the BBB by comparing the baseline physiologic signal to a physiologic signal obtained following a sonication burst of the ultrasound-based BBB opening procedure. For example, the processor circuitry 552 may determine a change in an physiologic signal during the ultrasound-based BBB opening procedure is indicative of opening or increased permeability of the BBB by recording the baseline physiologic signal prior to the ultrasound-based BBB opening procedure and by comparing features of the physiologic signal or derived parameters of the physiologic signal obtained during and/or post ultrasound-based BBB opening procedure to features or derived parameters of the baseline physiologic signal. The physiologic signal and baseline physiologic signal may be among the physiologic signals obtained from the patient, such as via sensor(s).

Figure 8:
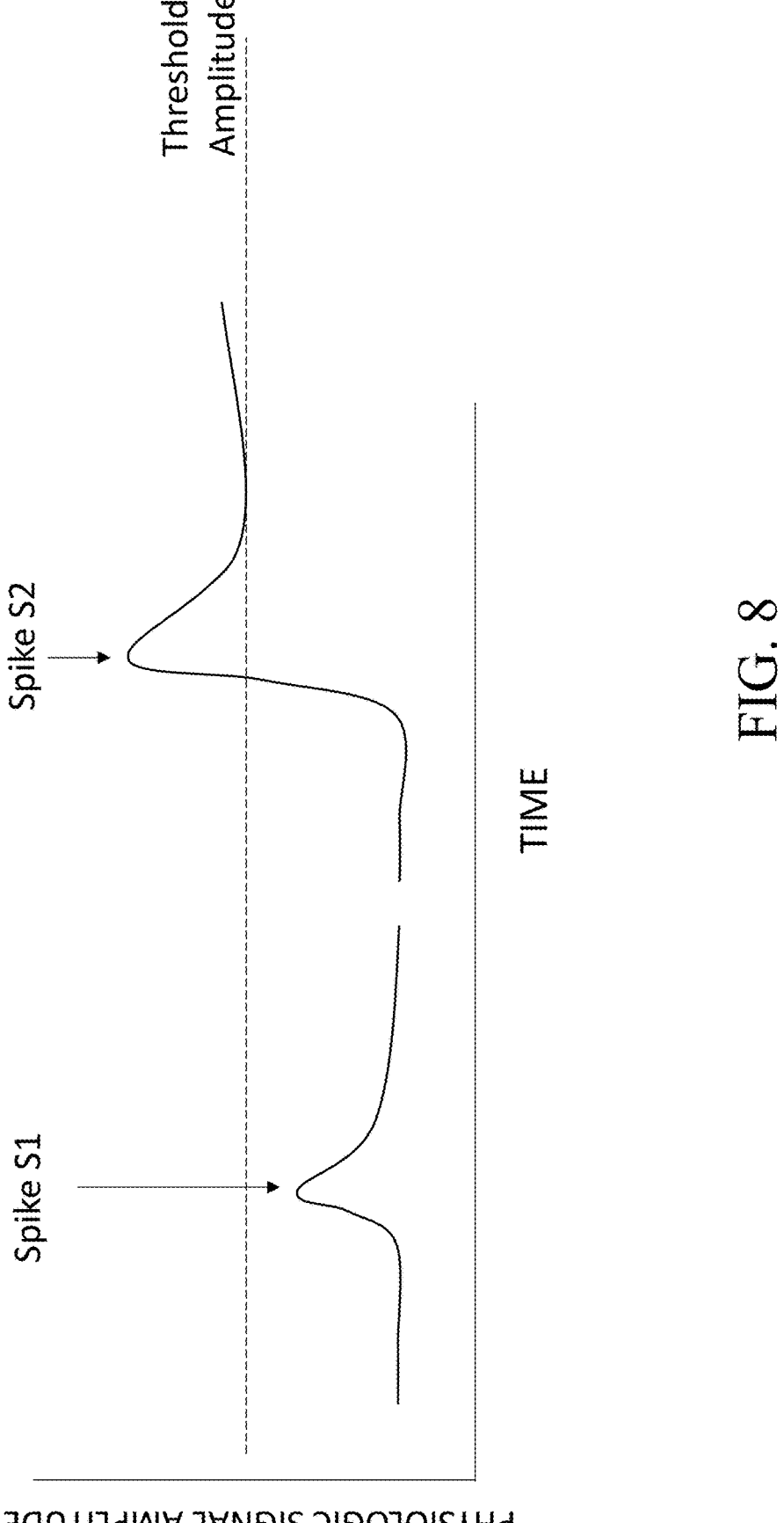
FIG. 8 illustrates example changes in a physiologic signal from a baseline level in response to an ultrasound-based BBB opening procedure compared to a threshold, according to examples of the present disclosure.

In some examples, the processor circuitry 552 may execute the instructions to control the ultrasound-based BBB opening procedure as a result of a change in the physiologic signals. For example, the control of the ultrasound-based BBB opening procedure may include stopping the ultrasound-based BBB opening procedure and/or allowing the ultrasound-based BBB opening procedure to continue depending on the change in the physiologic signals. For example, and as shown by FIG. 1, in response to an increase in the physiologic signal (e.g. a spike) above a threshold, the processor circuitry 552 may determine the BBB is opened and may stop the ultrasound-based BBB opening procedure. In response to no increase or an increase in the physiologic signal below the threshold, the processor circuitry 552 may continue the ultrasound-based BBB opening procedure. FIG. 8 shows this in more detail.

FIG. 8 illustrates example changes in a physiologic signal from a baseline level in response to an ultrasound-based BBB opening procedure compared to a threshold, according to examples of the present disclosure. In FIG. 8, the dashed line shows an example threshold level of a physiologic signal. In some examples, the threshold level is user-programmable. If the EEG (or other physiologic signal) amplitude stays below this threshold, as shown by Spike 1, while the ultrasound-based BBB opening procedure is ongoing, then the signal processing of the system and/or device (such as processing circuitry of system 200 of FIG. 2, device 550 of FIG. 5, and/or system 700 of FIG. 7) may be programmed to continue the ultrasound-based BBB opening procedure. If during the ultrasound-based BBB opening procedure, the EEG (or other physiologic signal) amplitude rises above this threshold, as shown by Spike 2, then the system and/or device can be programmed to end the ultrasound-based BBB opening procedure. Various logic conditions may be programmed to get different variations of the behavior of the system and/or device. For example, if Spike 2 only lasts for a few milliseconds (ms) above the threshold level, then the system and/or device may be programmed to continue the ultrasound-based BBB opening procedure. If Spike 2 lasts, for example, greater than 10 ms or the $T_{on}$ time (see FIG. 4), then the ultrasound-based BBB opening procedure may be terminated.

Figure 6:
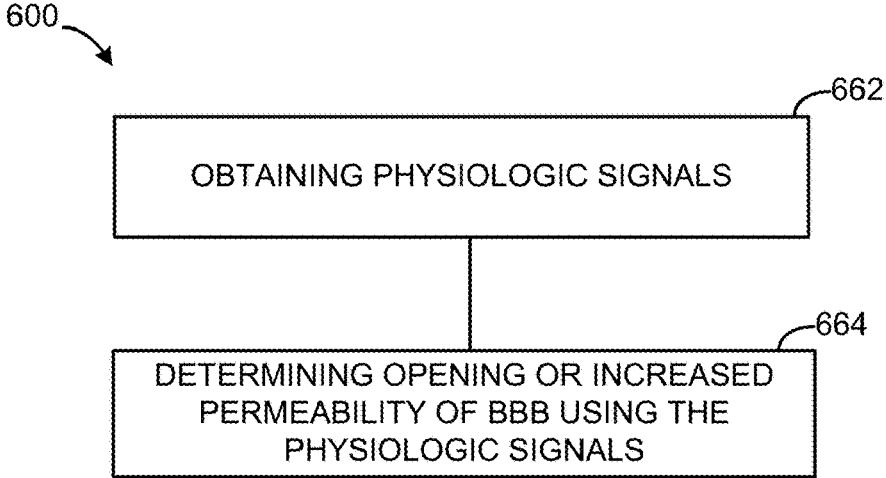
FIG. 6 is a flow chart of an example method for determining opening or increased permeability of the BBB using physiologic signals, according to examples of the present disclosure.

FIG. 6 is a flow chart of an example method for determining opening or increased permeability of the BBB using physiologic signals, according to examples of the present disclosure. The method may be implemented by the system of FIG. 2 or FIG. 7 or the device of FIG. 5, and/or may include an implementation of the method of FIG. 3.

At 662, the method 600 may include obtaining physiologic signals from a patient. The physiologic signals can include EEG signals, among other types of signals, and which can be captured using a physiological signal system, such as a sensor and optionally a physiologic signal analyzer as previously described in connection with FIG. 2.

In various examples, the physiologic signals may be obtained from the patient while the patient is undergoing the ultrasound-based BBB opening procedure performed by and/or using a FUS. For example, the method 600 may include obtaining at least portions of the physiologic signals during the ultrasound-based BBB opening procedure between sonication bursts of the ultrasound-based BBB opening procedure. In some examples, the method 600 may include obtaining at least portions of the physiologic signals prior to the ultrasound-based BBB opening procedure and during the ultrasound-based BBB opening procedure.

At 664, the method 600 may include determining opening or increased permeability of a BBB of the patient during an ultrasound-based BBB opening procedure using the physiologic signals. In some examples, the method 600 may include obtaining a baseline physiologic signal prior to the ultrasound-based BBB opening procedure and using the baseline physiologic signal to determine opening or increased permeability of the BBB by comparing the baseline physiologic signal to the physiologic signal obtained following a sonication burst of the ultrasound-based BBB opening procedure. For example, the method 600 may include determining a change in a physiologic signal during the ultrasound-based BBB opening procedure indicative of opening or increased permeability of the BBB by recording the baseline physiologic signal prior to the ultrasound-based BBB opening procedure and comparing features of the physiologic signal or derived parameters of the physiologic obtained during and/or post ultrasound-based BBB opening procedure to features or derived parameters of the baseline physiologic signal.

In some examples, the method 600 may include controlling the ultrasound-based BBB opening procedure as a result of a change in the physiologic signals. For example, controlling the ultrasound-based BBB opening procedure may include stopping the ultrasound-based BBB opening procedure and/or allowing the ultrasound-based BBB opening procedure to continue depending on the change in physiologic signals, as previously described.

Figure 7:
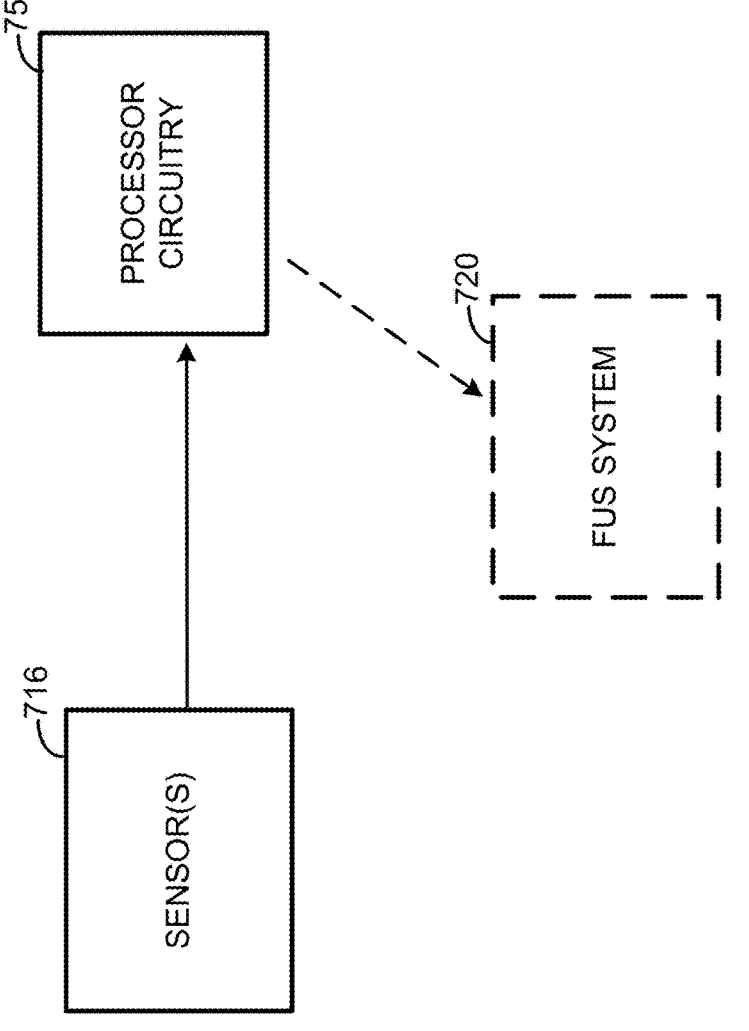
FIG. 7 illustrates an example system including a sensor and processor circuitry for determining opening or increased permeability of the BBB using physiologic signals, according to examples of the present disclosure.
Figure 7:

FIG. 7 illustrates an example system including a sensor and processor circuitry for determining opening or increased permeability of the BBB using physiologic signals, according to examples of the present disclosure. In some examples, the system 700 can include an example implementation of and/or include at least some the same features and attributes as the system 200 of FIG. 2. In some examples, the device 550 of FIG. 5 can form part of the system 700.

As shown by FIG. 7, the system 700 includes a sensor 716 and processor circuitry 752. The sensor 716 may be configured to capture physiologic signals from a patient. In some examples, the sensor 716 may include an implementation of a sensor of the system 200 of FIG. 2, such as an EEG sensor. For example, the physiologic signals can be EEG signals and the sensor 716 may include at least one EEG sensor. However, examples are not limited to EEG signals.

The processor circuitry 752 may be configured to obtain the physiologic signals from the sensor 716 and determine opening or increased permeability of a BBB of the patient during an ultrasound-based BBB opening procedure using the physiologic signals. In some examples, the processor circuitry 752 can include an implementation of processor circuitry 552 of the device 550 of FIG. 5.

In some examples, the processor circuitry 752 is configured to determine the opening or increased permeability of the BBB using the physiologic signals of the patient, at least portions of which are optionally obtained while the patient is undergoing the ultrasound-based BBB opening procedure performed by and/or using a FUS 720. For example, the processor circuitry 752 may be configured to obtain at least portions of the physiologic signals from the sensor 716 during the ultrasound-based BBB opening procedure between sonication bursts of the ultrasound-based BBB opening procedure. In some examples, the processor circuitry 752 may be configured to obtain at least portions of the physiologic signals from the sensor 716 prior to the ultrasound-based BBB opening procedure and during the ultrasound-based BBB opening procedure.

In some examples, the processor circuitry 752 is configured to obtain a baseline physiologic signal from the sensor 716 prior to the ultrasound-based BBB opening procedure and use the baseline physiologic signal to determine opening or increased permeability of the BBB by comparing the baseline physiologic signal to a physiologic signal obtained following a sonication burst of the ultrasound-based BBB opening procedure. For example, the processor circuitry 752 may be configured to determine a change in an physiologic signal during the ultrasound-based BBB opening procedure indicative of opening or increased permeability of the BBB by recording the baseline physiologic signal prior to the ultrasound-based BBB opening procedure and by comparing features of the physiologic signal or derived parameters of the physiologic obtained during and/or post ultrasound-based BBB opening procedure to features or derived parameters of the baseline physiologic signal.

In some examples, the system 700 may further include the FUS 720. The FUS 720 can be configured to open or increase the permeability of the BBB of the patient using a focused ultrasound. The FUS 720, as shown by FIG. 7 (as well as FIG. 1), may include at least some of substantially the same features and attributes, and/or otherwise be implemented, as described in U.S. Pat. No. 11,534,630, issued on Dec. 27, 2022, and entitled "Ultrasound Guided Opening of Blood-Brain Barrier", which is hereby incorporated herein by reference in its entirety for its teaching. For example, the FUS 720 may include an ultrasound cap for placement on the head of a patient, components for providing a contrast agent to the patient, a master controller having a processor for controlling the FUS 720 (which may form part of a controller device), and components for connecting the cap to the device (e.g. cable, cable interface). The ultrasound cap may include at some of substantially the same features and attributes, and/or otherwise be implemented, as described in more detail in US Publication No. 2023/0082109, published on Mar. 16, 2023, and entitled "Ultrasound Transducer Assembly", which is hereby incorporated herein by reference in its entirety for its teaching. In brief, the ultrasound cap may include several types of transducer components: (1) a low-frequency transducer configured to provide the energy to open the blood-brain barrier, (2) a high-frequency transducer set or imaging array configured to image through the thin areas of the skull to image structures of the brain; the ultrasound images obtained from the high-frequency set may be aligned with the images obtained from another modality such as MRI where the energy for imaging can penetrate the skull, and/or (3) monitoring transducers which may be used in a feedback loop to open the BBB. In various embodiments, the monitoring transducers may be used to provide safe opening of the BBB, by capturing or receiving signals coming from structures within the brain and presenting these signals for further analysis by other components of the FUS 720.

For the purposes of this disclosure, in some embodiments, the low-frequency range may be between 0.200 MHz to 10 MHz and, in some embodiments, may be between 0.25 MHz to 5 MHz. The high-frequency range may be between 2 MHz to 5 MHz, for example. The monitoring transducers may operate with a bandwidth 100 kHz to 10 MHz, for example.

In some examples, the processor circuitry 752 is configured to control the ultrasound-based BBB opening procedure as a result of a change in the physiologic signals. As previously described, the control may include stopping the ultrasound-based BBB opening procedure and/or allowing the ultrasound-based BBB opening procedure to continue depending on the change in physiologic signals and via communication with the FUS 720.

Unless the context clearly requires otherwise, throughout the description and the claims: "comprise", "comprising", and the like are to be construed in an inclusive sense, as opposed to an exclusive or exhaustive sense; that is to say, in the sense of "including, but not limited to"; "connected", "coupled", or any variant thereof, means any connection or coupling, either direct or indirect, between two or more elements; the coupling or connection between the elements can be physical, logical, or a combination thereof; "herein", "above", "below", and words of similar import, when used to describe this specification, shall refer to this specification as a whole, and not to any particular portions of this specification; "or", in reference to a list of two or more items, covers all of the following interpretations of the word:

any of the items in the list, all of the items in the list, and any combination of the items in the list; and singular forms "a", "an", and "the" also include the meaning of any appropriate plural forms.

Words that indicate directions such as vertical", "transverse", "horizontal", "upward", "downward", "forward", "backward", "inward", "outward", "left", "right", "front", "back", "top", "bottom", "below", "above", and "under", among others, used in this description and any accompanying claims (where present), depend on the specific orientation of the device and/or system described and illustrated. The subject matter described herein may assume various alternative orientations. Accordingly, directional terms are not strictly defined and should not be interpreted narrowly.

Examples described herein may be implemented using specifically designed hardware, configurable hardware, programmable data processors configured by software (which may optionally comprise "firmware") executable on the data processors (e.g. processor circuitry), special purpose computers or data processors that are specifically programmed, configured, or constructed to perform at least a portion of a method described above and/or combinations thereof. For example, the FUS, the EEG (or other physiologic signal) analyzer and other components of the EEG system (or other physiologic signal system), and/or the master controller may include specifically designed hardware. Example specifically designed hardware includes logic circuits, application-specific integrated circuits (ASICs), large scale integrated circuits (LSIs), very large scale integrated circuits (VLSIs), among others. Examples of configurable hardware are: at least one programmable logic device such as programmable array logic (PALs), programmable logic arrays (PLAs), and field programmable gate arrays (FPGAs). Examples of programmable data processors are: microprocessors, digital signal processors (DSPs), embedded processors, graphics processors, math co-processors, general purpose computers, server computers, cloud computers, mainframe computers, and/or computer workstations, among others. For example, at least data processor in a control circuit for a system may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

For example, while processes or blocks are presented in a given order, alternative examples may perform routines having steps, or employ systems having blocks, in a different order, and some processes or blocks may be deleted, moved, added, subdivided, combined, and/or modified to provide alternative or sub-combinations. Each of these processes or blocks may be implemented in a variety of different ways. Also, while processes or blocks are at times shown as being performed in series, these processes or blocks may instead be performed in parallel, or may be performed at different times.

In addition, while elements are at times shown as being performed sequentially, they may be performed simultaneously or in different sequences. It is therefore intended that the following claims are interpreted to include all such variations as are within their intended scope.

Software and other modules may reside on servers, workstations, personal computers, tablet computers, image data encoders, image data decoders, personal digital assistants (PDAs), color-grading tools, video projectors, audio-visual receivers, displays (such as televisions), digital cinema projectors, media players, and other devices suitable for the methods described herein. Aspects of the system can be practiced with other communications, data processing, or computer system configurations, including: Internet appliances, hand-held devices (including PDAs), wearable computers, all manner of cellular or mobile phones, multiprocessor systems, microprocessor-based or programmable consumer electronics (e.g. video projectors, audio-visual receivers, displays, such as televisions), set-top boxes, color-grading tools, network PCs, mini-computers, and mainframe computers, among others.

Examples may be provided in the form of a program product. The program product may comprise any non-transitory medium which carries a set of computer-readable instructions which, when executed by processor, cause the processor to execute a method described herein. Program products may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or pre-programmed chips (e.g. EEPROM semiconductor chips), or nanotechnology memory, among others. The computer-readable signals on the program product may optionally be compressed or encrypted.

Various examples may be implemented in software. For greater clarity, "software" includes any instructions executed on a processor, and may include (but is not limited to) firmware, resident software, and/or microcode, among others. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. a software module, processor, assembly, device, circuit, etc.) is referred to above, unless otherwise indicated, reference to that component should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific example systems, methods, and devices are described herein for purposes of illustration. These are only examples. Examples can be applied to systems and devices other than the example systems described above, as well as variations and modification to the systems, devices, and methods described herein. Examples variations include: replacing features, elements and/or acts with equivalent features, elements and/or acts; mixing and matching of features, elements and/or acts from different embodiments; combining features, elements and/or acts from examples as described herein with features, elements and/or acts of other technology; and/or omitting combining features, elements and/or acts from described examples.

Various features are described as being present in "some or various examples". Such features are not mandatory and may not be present in all examples. Examples may include zero, any one, or any combination of two or more of such features. This is limited only to the extent that certain ones of such features are incompatible with other ones of such features in the sense that it would be impossible for a person of ordinary skill in the art to construct a practical embodiment that combines such incompatible features. Consequently, the description that "some (or various) examples" include feature A and "some (or various) examples" includes feature B should be interpreted as an express indication that other examples combine features A and B (unless the description states otherwise or features A and B are fundamentally incompatible).

The invention claimed is:

1. A device comprising:

memory circuitry that stores a set of non-transitory instructions; and processor circuitry coupled to the memory circuitry and in communication with a sensor configured to capture physiologic signals from a patient and communicate the physiological signals to the processor circuitry and a focused ultrasound system (FUS), the processor circuitry being configured to execute the instructions to:

determine opening or increased permeability of a blood-brain barrier (BBB) of the patient during an ultrasound-based BBB opening procedure performed by the FUS by monitoring energy in predefined bands of frequency within the physiologic signals, as received from the sensor, for a change in the physiologic signals; and in response, control the ultrasound-based BBB opening procedure as a result of the change in the physiologic signals.

2. The device of claim 1, wherein the processor circuitry is configured to execute the instructions to determine the opening or the increased permeability of the BBB using the physiologic signals of the patient, at least portions of which are obtained while the patient is undergoing the ultrasound-based BBB opening procedure performed by the FUS.

3. The device of claim 1, wherein the processor circuitry is configured to execute the instructions to determine the opening or increased permeability of the BBB by monitoring the energy further includes instructions executed to:

divide a frequency spectrum of the physiologic signals into bins of a defined frequency width, at least one of the bins being defined by the predefined bands of frequency;

sum the energy values in each bin and index the energy values by sonication burst number and type;

average the energy values for each bin across multiple sonication bursts;

compare the average energy values to a reference value associated with a baseline physiological signal obtained prior to the ultrasound-based BBB opening procedure or between sonication bursts; and determine the change in the physiologic signals is caused by opening or increased permeability of the BBB or not based on the comparison.

4. The device of claim 3, wherein the processor circuitry is configured to execute the instructions to:

determine the change in the physiologic signals is caused by opening or increased permeability of the BBB or not including:

determine the change in the physiologic signals is caused by opening or increased permeability of the BBB in response to the average energy values in the at least one bin defined by the predefined bands of frequency having a change in energy value outside a threshold of the reference value and the average energy values of the remaining bins being within the threshold of the reference value; and determine the BBB has not opened or increased permeability in response to the average energy values in the at least one bin defined by the predefined bands of frequency having no change or a change in energy value within the threshold of the reference value or average energy values in all bins having the change in energy value outside the threshold of the reference value;

control the ultrasound-based BBB opening procedure by instructing the FUS to:

stop the ultrasound-based BBB opening procedure in response to the determination that the BBB has opened or increased permeability; and in response to the determination that the BBB has not opened or increased permeability, at least one of:

continue the ultrasound-based BBB opening procedure; and adjust a sonication parameter including at least one of excitation voltage and sonication burst time.

5. The device of claim 1, wherein the physiologic signals are electroencephalography (EEG) signals and the processor circuitry is configured to execute the instruction to determine the change in the physiologic signals is caused by opening or increased permeability of the BBB or not includes instructions executable to monitor the energy in the predefined bands of frequency within the physiologic signals obtained from the patient as received from the sensor for the change in the physiologic signals which includes energy changes in the predefined bands of frequency following sonication bursts during the ultrasound-based BBB opening procedure as compared to energy in the predefined bands of frequency without sonication burst applied.

6. The device of claim 1, wherein the processor circuitry is configured to execute the instructions to obtain at least portions of the physiologic signals during the ultrasound-based BBB opening procedure between sonication bursts of the ultrasound-based BBB opening procedure.

7. The device of claim 1, wherein the processor circuitry is configured to execute the instructions to obtain at least portions of the physiologic signals prior to the ultrasound-based BBB opening procedure and during the ultrasound-based BBB opening procedure.

8. The device of claim 1, wherein the processor circuitry is configured to execute the instructions to obtain a baseline physiologic signal prior to the ultrasound-based BBB opening procedure and use the baseline physiologic signal to determine opening or increased permeability of the BBB by comparing the baseline physiologic signal to respective ones of the physiologic signals obtained following a sonication burst of the ultrasound-based BBB opening procedure.

9. The device of claim 1, wherein the processor circuitry is configured to execute the instructions to determine the change in the physiologic signals during the ultrasound-based BBB opening procedure indicative of opening or increased permeability of the BBB by recording a baseline physiologic signal prior to the ultrasound-based BBB opening procedure and by comparing features of the physiologic signals or derived parameters of the physiologic signals obtained during and/or post ultrasound-based BBB opening procedure to features or derived parameters of the baseline physiologic signal.

10. A method comprising:

obtaining physiologic signals from a patient by a sensor configured to capture the physiologic signals and communicate the physiological signals to processor circuitry; and determining, via the processor circuitry, opening or increased permeability of a blood-brain barrier (BBB) of the patient during an ultrasound-based BBB opening procedure as performed by a focused ultrasound system (FUS) by monitoring energy in predefined bands of frequency within the physiologic signals for a change in the physiologic signals; and in response, controlling, via the processor circuitry in communication with the FUS, the ultrasound-based BBB opening procedure as performed by the FUS as a result of the change in the physiologic signals.

11. The method of claim 10, including obtaining the physiologic signals from the patient while the patient is undergoing the ultrasound-based BBB opening procedure performed by and/or using the FUS.

12. The method of claim 10, wherein controlling the ultrasound-based BBB opening procedure includes:

in response to determining the BBB has opened or increased permeability, stopping the ultrasound-based BBB opening procedure as performed by the FUS prior to a preprogrammed sonication duration; and in response to determining the BBB has not opened or increased permeability, at least one of:

continuing the ultrasound-based BBB opening procedure to an end of the preprogrammed sonication duration or extending the preprogrammed sonication duration, and adjusting a sonication parameter including at least one of excitation voltage and sonication burst time.

13. The method of claim 10, including obtaining at least portions of the physiologic signals during the ultrasound-based BBB opening procedure between sonication bursts of the ultrasound-based BBB opening procedure.

14. The method of claim 10, including obtaining at least portions of the physiologic signals prior to the ultrasound-based BBB opening procedure and during the ultrasound-based BBB opening procedure, the method including:

determining the opening or increased permeability of the BBB by:

dividing a frequency spectrum of the physiologic signals into bins of a defined frequency width, at least one of the bins being defined by the predefined bands of frequency;

summing the energy values in each bin, indexing the energy values by sonication burst number and type, and averaging the energy values for each bin across multiple sonication bursts;

comparing the average energy values to a baseline physiological signal associated with the at least portions of the physiologic signals obtained prior to the ultrasound-based BBB opening procedure; and determining the change in the physiologic signals is caused by opening or increased permeability of the BBB or not based on the comparison by:

determining the change in the physiologic signals is caused by opening or increased permeability of the BBB in response to the average energy values in the at least one bin defined by the predefined bands of frequency and associated with the at least portion of physiologic signals obtained during the ultrasound-based BBB opening procedure having a change in energy value outside a threshold of the baseline physiological signal and the average energy values of the remaining bins being within the threshold of the baseline physiological signal; and determining the BBB has not opened or increased permeability in response to the average energy values in the at least one bin defined by the predefined bands of frequency having no change or a change in energy value within the threshold of the baseline physiological signal or average energy values in all bins and associated with the at least portion of physiologic signals obtained during the ultrasound-based BBB opening procedure having the change in energy value outside the threshold of the baseline physiological signal.

15. The method of claim 10, including obtaining a baseline physiologic signal prior to the ultrasound-based BBB opening procedure and using the baseline physiologic signal to determine opening or increased permeability of the BBB by comparing the baseline physiologic signal to the physiologic signal obtained following a sonication burst of the ultrasound-based BBB opening procedure.

16. A system comprising:

a sensor configured to capture physiologic signals from a patient;

a focused ultrasound system (FUS) configured to open or increase permeability of a blood-brain barrier (BBB) of the patient using a focused ultrasound; and processor circuitry in communication with the sensor and the FUS and being configured to:

obtain the physiologic signals from the sensor; and determine opening or increased permeability of the BBB of the patient during an ultrasound-based BBB opening procedure using the physiologic signals received from the sensor during the ultrasound-based BBB opening procedure; and control the ultrasound-based BBB opening procedure as performed by the FUS as a result of a change in the physiologic signals obtained during the ultrasound-based BBB opening procedure.

17. The system of claim 16, wherein the processor circuitry is configured to determine the opening or increased permeability of the BBB by monitoring energy in predefined bands of frequency within the physiologic signals for the change in the physiologic signals.

18. The system of claim 17, wherein the processor circuitry is configured to determine the opening or increased permeability of the BBB using physiologic signals of the patient, at least portions of which are obtained while the patient is undergoing the ultrasound-based BBB opening procedure performed by the focused ultrasound FUS and to monitor the energy including:

dividing a frequency spectrum of the physiologic signals into bins of a defined frequency width, at least one of the bins being defined by the predefined bands of frequency;

summing the energy values in each bin and index the energy values by sonication burst number and type;

averaging the energy values for each bin across multiple sonication bursts;

comparing the average energy values to a reference value associated with a baseline physiological signal obtained prior to the ultrasound-based BBB opening procedure or between sonication bursts; and determining the change in the physiologic signals is caused by opening or increased permeability of the BBB or not based on the comparison.

19. The system of claim 16, wherein the processor circuitry is configured to control the ultrasound-based BBB opening procedure by instructing the FUS to:

stop the ultrasound-based BBB opening procedure as performed by the FUS prior to a preprogrammed sonication duration in response to determining that the BBB has opened or increased permeability; and at least one of:

continue the ultrasound-based BBB opening procedure to an end of the preprogrammed sonication duration or extending the preprogrammed sonication duration in response to determining that the BBB has not opened or increased permeability; and adjust a sonication parameter including at least one of excitation voltage and sonication burst time in response to determining that the BBB has not opened or increased permeability.

20. The system of claim 16, wherein the processor circuitry is configured to obtain a baseline physiologic signal from the sensor prior to the ultrasound-based BBB opening procedure and use the baseline physiologic signal to determine opening or increased permeability of the BBB by comparing the baseline physiologic signal to a physiologic signal obtained following a sonication burst of the ultrasound-based BBB opening procedure.

* * * * *